United States Patent
Chen et al.

(10) Patent No.: US 7,157,424 B2
(45) Date of Patent: *Jan. 2, 2007

(54) PHARMACEUTICAL COMPOSITIONS FOR HEPATITIS C VIRAL PROTEASE INHIBITORS

(75) Inventors: Shirlynn Chen, Somers, NY (US); Xiaohui Mei, Highland Mills, NY (US); Zeren Wang, Southbury, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 162 days.

This patent is subject to a terminal disclaimer.

(21) Appl. No.: 10/807,023

(22) Filed: Mar. 23, 2004

(65) Prior Publication Data

US 2004/0229776 A1    Nov. 18, 2004

Related U.S. Application Data

(60) Provisional application No. 60/459,765, filed on Apr. 2, 2003.

(51) Int. Cl.
*A61K 38/12* (2006.01)
*A61K 38/00* (2006.01)
*A61K 38/02* (2006.01)
*A61K 31/4709* (2006.01)

(52) U.S. Cl. .................. 514/11; 514/2; 514/9; 514/312

(58) Field of Classification Search .................. None
See application file for complete search history.

(56) References Cited

U.S. PATENT DOCUMENTS 6,231,887 B1    5/2001  Gao et al.
6,608,027 B1    8/2003  Tsantrizos et al.
6,828,301 B1 *  12/2004 Chen et al. ..................... 514/9
2001/0024658 A1 * 9/2001 Chen et al. ................ 424/452
2003/0195228 A1  10/2003 Chen et al.
2005/0080005 A1  4/2005  Llinas-Brunet et al.

FOREIGN PATENT DOCUMENTS

WO   WO 99/06044 A1   2/1999
WO   WO 00/59929 A1   10/2000
WO   WO 03/066103 A1  8/2003

OTHER PUBLICATIONS

Captex(R) 355 Product Sheet, version 6. ABITEC Corp.. Jul. 28, 2004. 2 pages.*

* cited by examiner

*Primary Examiner*—Cecilia J. Tsang
*Assistant Examiner*—Andrew D. Kosar
(74) *Attorney, Agent, or Firm*—Michael P. Morris; Mary Ellen Devlin; Philiip I. Datlow

(57) ABSTRACT

Disclosed are pharmaceutical compositions of hepatitis C viral protease inhibitors, and methods of using these compositions for inhibiting the replication of the hepatitis C virus (HCV) and for the treatment of an HCV infection. These compositions are lipid based systems and comprise the hepatitis C viral protease inhibitor together with at least one pharmaceutically acceptable amine, at least one pharmaceutically acceptable base, at least one pharmaceutically acceptable oil and optionally one or more additional ingredients.

29 Claims, 2 Drawing Sheets

PHARMACEUTICAL COMPOSITIONS FOR HEPATITIS C VIRAL PROTEASE INHIBITORS

This application claims benefit to U.S. Provisional Application No. 60/459,765, filed Apr. 2, 2003, which application is herein incorporated by reference in its entirety.

FIELD OF THE INVENTION

The present invention relates in general to pharmaceutical compositions of hepatitis C viral protease inhibitors, methods of using these compositions for inhibiting the replication of the hepatitis C virus (HCV) and for the treatment of an HCV infection.

BACKGROUND OF THE INVENTION

It has recently been discovered that certain macrocyclic compounds are potent and specific inhibitors of hepatitis C virus (HCV) protease. In particular, compounds of the following formula I have been found to be an especially potent class of inhibitors against the NS3 serine protease of HCV:

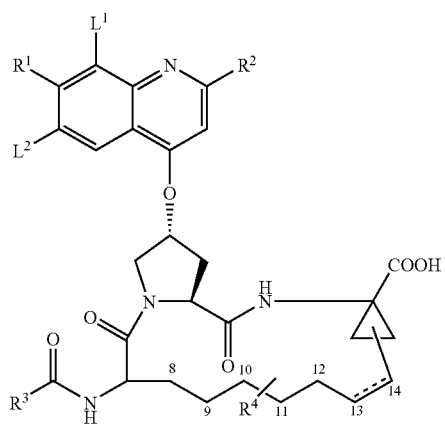

(I)

wherein:
— designates an optional bond forming a double bond between positions 13 and 14;
$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
$L^1$, $L^2$ are each independently H, halogen, $C_{1-4}$alkyl, —O—$C_{1-4}$alkyl, or —S—$C_{1-4}$alkyl (the sulfur being in any oxidized state);
$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\ or\ 10}$ aryl or Het, wherein Het is a five-, six-, or seven-membered saturated or unsaturated heterocycle containing from one to four ring heteroatoms selected from nitrogen, oxygen and sulfur;
said cycloalkyl, aryl or Het being optionally substituted with $R^6$,
wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;
or $R^6$ is NH—C(O)—$OR^8$ wherein $R^8$ is $C_{1-6}$ alkyl or $C_{3-6}$ cycloalkyl;
$R^3$ is $R^9O$— or $R^9NH$—, wherein $R^9$ is $C_{1-6}$alkyl or $C_{3-6}$cycloalkyl;
$R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

See Tsantrizos et al., U.S. application Ser. No. 09/760,946, filed on Jan. 16, 2001, now U.S. Pat. No. 6,608,027 B1 (Boehringer Ingelheim (Canada), Ltd.), which is herein incorporated by reference in its entirety and is hereinafter referred to as "Tsantrizos et al". See also the corresponding WO 00/59929. In addition, see Llinas-Brunet, U.S. Provisional Application No. 60/504,839, filed on Sep. 22, 2003, which is herein incorporated by reference in its entirety and is hereinafter referred to as "Llinas-Brunet".

A structural feature of the compounds of formula I is the presence of the C-terminal carboxylic acid functionality, which was shown to be responsible not only for the potency and reversibility observed for this inhibitor series, but also for the excellent specificity for HCV protease compared to other serine/cysteine proteases. An HCV serine protease inhibitor such as the compounds of formula I would be expected to be an antiviral agent acting via a novel mechanism, i.e. blockage of a virus-encoded essential function for HCV replication. A drug acting through this mechanism should suppress viral replication of all HCV genotypes and therefore provide tangible benefits to patients with chronic hepatitis C.

A common problem among protease inhibitors is that these compounds are lipophilic and have low aqueous solubility. Because of the poor aqueous solubility, conventional solid and liquid pharmaceutical preparations containing these inhibitors may not be absorbed by the patient in a satisfactory manner. Of the various factors that can affect the bioavailability of a drug when administered orally, (which include aqueous solubility, drug absorption through the gastrointestinal tract, dosage strength and first pass effect), aqueous solubility is often found to be among the most important factors. Poorly water soluble compounds often exhibit either erratic or incomplete absorption in the digestive tract, and thus produce a less than desirable response.

The compounds of formula I are zwitterionic and are capable of forming salts with strong acids and bases. Attempts to identify salts of such compounds in solid forms, which would substantially improve aqueous solubility, have not been successful. Various salts of these compounds have been found to be very hygroscopic, reducing the stability of the compounds. In addition, formulations of salts of these compounds generally are prone to precipitation of the parent free-acid in the gastrointestinal tract. Representative compounds of formula I have shown poor bioavailability when administered to animals as an aqueous suspension, suggesting that conventional formulations containing these inhibitors may not be absorbed in a satisfactory manner. Thus, there is a need in the art for pharmaceutical compositions of the formula I compounds having improved bioavailability.

Methods of formulating certain lipophilic macrocyclic compounds into pharmaceutical formulations have been previously reported. For example, Cavanak, U.S. Pat. No. 4,388,307, discloses the preparation of emulsified formulations of commercially available cyclosporins, and Hauer et.al, U.S. Pat. No. 5,342,625, and Meizner et al. WO 93/20833 disclose the preparation of cyclosporin microemulsions and microemulsion pre-concentrates. Komiya et.

al, U.S. Pat. No. 5,504,068, further discloses the preparation of an enhanced topical formulations of cyclosporin.

Examples of "self-emulsifying" formulations of lipophilic compounds include Lipari et al, WO 96/36316, which discloses a self-emulsifying pre-concentrate comprising a lipophilic compound, d-alpha-tocopheryl polyethylene glycol 1000 succinate (TPGS) and a lipophilic phase. Gao et al., U.S. Pat. No. 6,121,313 discloses a self-emulsifying formulation of a pyranone protease inhibitor comprising the pyranone compound, a mixture of mono- and di-glycerides, one or more solvents and one or more surfactants; and Gao et al, U.S. Pat. No. 6,231,887 B1 discloses a self-emulsifying formulation of a pyranone protease inhibitor comprising the pyranone compound, an amine, one or more solvents and one or more surfactants.

Yu et. al U.S. Pat. Nos. 5,360,615 and 5,071,643 disclose the preparation of a solvent system for enhancing the solubility of acidic, basic or amphoteric compounds by partial ionization comprising a mixture of polyethylene glycol, hydroxide or hydrogen ion, and water. Morton et al U.S. Pat. No. 5,376,688 discloses solutions of acidic, basic or amphoteric pharmaceutical agents comprising the pharmaceutical agent, an ionic species and a solvent system. Bhagwat et. al U.S. Pat. No. 6,056,977 teaches the use of polysaccharide based matrix for sustained release of a sulfonylurea.

A self-emulsifying drug delivery system (SEDDS) having improved bioavailability has recently been developed for the compounds of formula (I), as described in U.S. application Ser. No. 10/357,919 (S. Chen et al.), filed Feb. 4, 2003, now U.S. Pat. No. 6,828,301, and in PCT/US03/03380 (Boehringer Ingelheim Pharmaceuticals, Inc.), filed Feb.5, 2003, published as WO 03/066103 A1. This formulation comprises a compound of formula (I), about 0.1 to 10% by weight of a pharmaceutically acceptable amine or a mixture of pharmaceutically acceptable amines, one or more pharmaceutically acceptable oils, optionally one or more pharmaceutically acceptable hydrophilic solvents, optionally one or more pharmaceutically acceptable polymers, and optionally one or more pharmaceutically acceptable surfactants. However, it has been found that this formulation may not be fully optimized with respect to its chemical stability and therefore may require storage under refrigerated conditions.

BRIEF SUMMARY OF THE INVENTION

The present invention overcomes the aforementioned problems by providing pharmaceutical compositions of the formula I compounds having acceptable bioavailability and also improved chemical stability as compared to the previous SEDDS formulation.

The pharmaceutical compositions of the present invention all comprise a compound of formula I together with one or more pharmaceutically acceptable amines, bases and oils. The compositions of the present invention may optionally include one or more additional ingredients, e.g., pharmaceutically acceptable solvents, surfactants, polymers, etc., as will be discussed in more detail below. The present invention is also directed to the methods of manufacturing these compositions, as described hereinafter.

In a general embodiment, the pharmaceutical composition of the present invention comprises:

(a) a compound of formula (I):

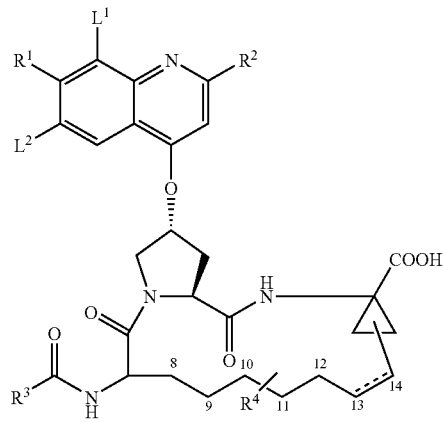

wherein:
— designates an optional bond forming a double bond between positions 13 and 14;

$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;

$L^1$, $L^2$ are each independently H, halogen, $C_{1-4}$alkyl, —O—$C_{1-4}$alkyl, or —S—$C_{1-4}$alkyl (the sulfur being in any oxidized state);

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_6$ or 10 aryl or Het, wherein Het is a five-, six-, or seven-membered saturated or unsaturated heterocycle containing from one to four ring heteroatoms selected from nitrogen, oxygen and sulfur;

said cycloalkyl, aryl or Het being optionally substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;

or $R^6$ is NH—C(O)—$OR^8$ wherein $R^8$ is $C_{1-6}$ alkyl or $C_{3-6}$ cycloalkyl;

$R^3$ is $R^9$O— or $R^9$NH—, wherein $R^9$ is $C_{1-6}$ alkyl or $C_{3-6}$cycloalkyl;

$R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

or a tautomer thereof;

(b) about 0.1 to 10% by weight of a pharmaceutically acceptable amine or a mixture of pharmaceutically acceptable amines;

(c) about 0.1 to 10% by weight of a pharmaceutically acceptable base or a mixture of pharmaceutically acceptable bases;

(d) one or more pharmaceutically acceptable oils;

(e) optionally one or more pharmaceutically acceptable hydrophilic solvents;

(f) optionally one or more pharmaceutically acceptable polymers; and (g) optionally one or more pharmaceutically acceptable surfactants;

Another important aspect of the present invention involves a method of inhibiting the replication of hepatitis C virus by exposing the virus to a hepatitis C viral NS3 protease-inhibiting amount of a pharmaceutical composition of the present invention.

Another important aspect of the present invention involves a method of treating a hepatitis C viral infection in a mammal by administering to the mammal in need thereof a therapeutically effective amount of a pharmaceutical composition of the present invention.

DETAILED DESCRIPTION OF THE INVENTION

Definition of Terms and Conventions Used

Figure 1:
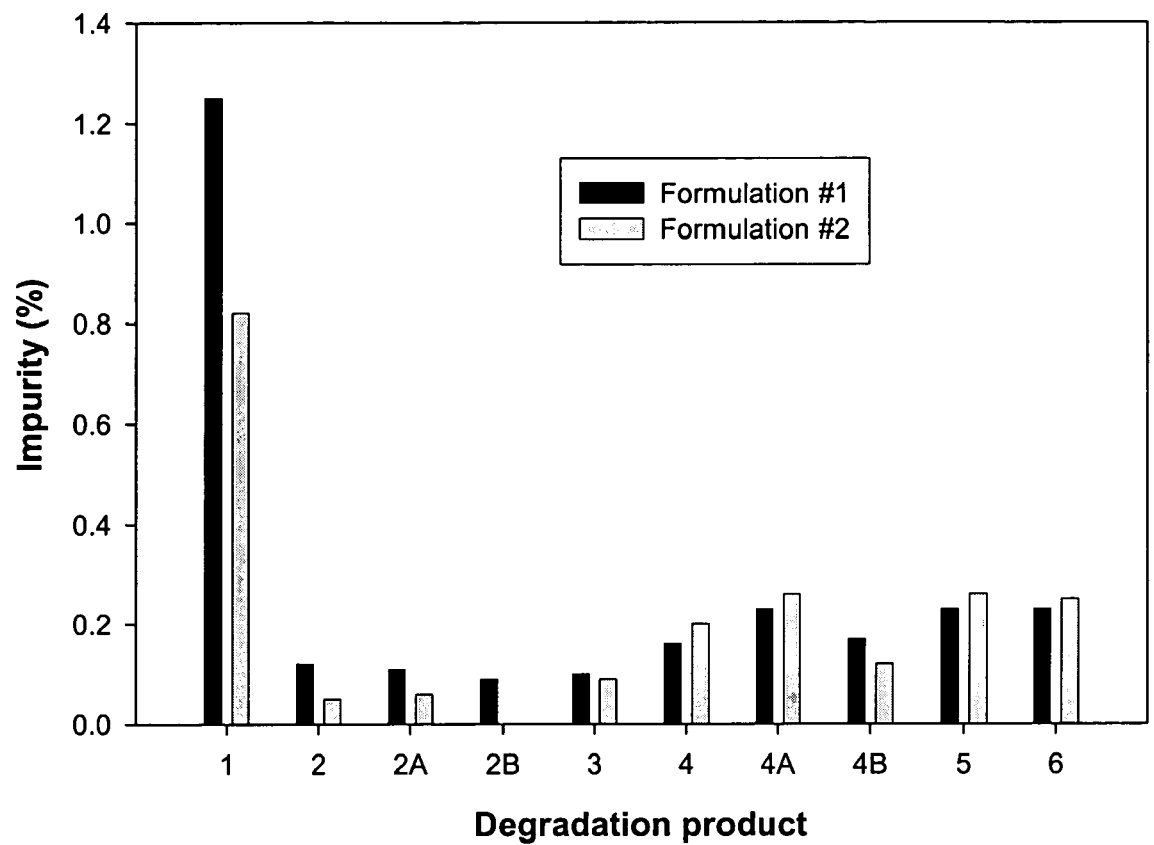
FIG. 1 shows the impurity profile of a formulation according to the present invention containing tromethamine and sodium hydroxide (Formulation #2 and a comparative formulation without sodium hydroxide (Formulation #1) when both formulations were subjected to stability testing for 5 days at 70° C. This figure shows that the level of major degration product 1 is lower in Formulation #2 than in comparative Formulation #1.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

A. Chemical and Pharmaceutical Nomenclature, Terms, and Conventions

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

The term "$C_{1-6}$ alkyl" as used herein, either alone or in combination with another substituent, means acyclic, straight or branched chain alkyl substituents containing from 1 to six carbon atoms and includes, for example, methyl, ethyl, propyl, butyl, hexyl, 1-methylethyl, 1-methylpropyl, 2-methylpropyl, and 1,1-dimethylethyl.

The term "$C_{3-6}$ cycloalkyl" as used herein, either alone or in combination with another substituent, means a cycloalkyl substituent containing from three to six carbon atoms and includes cyclopropyl, cyclobutyl, cyclopentyl, and cyclohexyl.

The term "$C_{1-6}$ alkoxy" as used herein, either alone or in combination with another substituent, means the substituent $C_{1-6}$ alkyl-O— wherein alkyl is as defined above containing up to six carbon atoms. Alkoxy includes methoxy, ethoxy, propoxy, 1-methylethoxy, butoxy and 1,1-dimethylethoxy. The latter substituent is known commonly as tert-butoxy.

The term "$C_{3-6}$ cycloalkoxy" as used herein, either alone or in combination with another substituent, means the substituent $C_{3-6}$ cycloalkyl-O— containing from 3 to 6 carbon atoms.

The term "halo" as used herein means a halogen substituent selected from bromo, chloro, fluoro or iodo.

The term "haloalkyl" as used herein means as used herein, either alone or in combination with another substituent, means acyclic, straight or branched chain alkyl substituents having one or more hydrogens substituted for a halogen selected from bromo, chloro, fluoro or iodo.

The term "thioalkyl" as used herein means as used herein, either alone or in combination with another substituent, means acyclic, straight or branched chain alkyl substituents containing a thiol (HS) group as a substituent. An example of a thioalkyl group is a thiopropyl, e.g., HS—$CH_2CH_2CH_2$— is one example of a thiopropyl group.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl—ring system.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

The term "Het" also includes a heterocycle as defined above fused to one or more other cycle be it a heterocycle or any other cycle. One such examples includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic system include: quinoline, indole, pyridine,

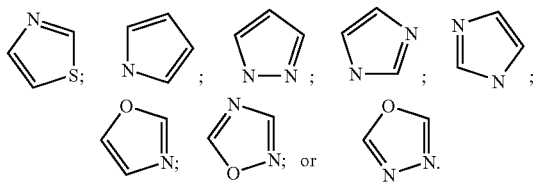

The term "oxo" means the double-bonded group (=O) attached as a substituent.

The term "thio" means the double-bonded group (=S) attached as a substituent.

The term "compounds of the invention", and equivalent expressions, are meant to embrace compounds of Formula (I) as herein described, including the tautomers and isomers thereof, where the context so permits. In general, the compounds of the invention and the formulas designating the compounds of the invention are understood to only include the stable compounds thereof and exclude unstable compounds, even if an unstable compound might be considered to be literally embraced by the compound formula.

The term "stable compound" means a compound that is sufficiently robust to survive isolation to a useful degree of purity from a reaction mixture and formulation into an efficacious pharmaceutical composition. For example, a compound which would have a "dangling valency" or is a "carbanion" is not a compound contemplated by the invention.

The term "pharmaceutical composition of the invention" and equivalent expressions is meant to embrace all the various types of pharmaceutical compositions as described hereinafter, unless it is clear from the context that reference is being made to a particular type of pharmaceutical composition within the scope of the present invention.

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "semi-solid" means a material that is neither solid (elastic behavior) nor liquid (viscous behavior) and possesses the characteristics of both viscosity and elasticity. Examples of semi-solid materials include gels, ointments, creams, and highly viscous liquids.

The term "about" means within 20%, preferably within 10%, and more preferably within 5% of a given value or range. For example, "about 10%" means from 8% to 12%, preferably from 9% to 11%, and more preferably from 9.5% to 10.5%. When the term "about" is associated with a range of values, e.g., "about X to Y %", the term "about" is intended to modify both the lower (X) and upper (Y) values of the recited range. For example, "about 0.1 to 10%" is equivalent to "about 0.1% to about 10%".

All percentages recited for amounts of ingredients in the compositions are percentages by weight with respect to the whole composition.

B. Isomer Terms and Conventions

The terms "isomers" or "stereoisomers" mean compounds having the same number and kind of atoms, and hence the same molecular weight, but differing in respect to the arrangement or configuration of the atoms in space. The term includes optical isomers and geometric isomers.

The term "optical isomer" means a stable isomer that has at least one chiral atom or restricted rotation giving rise to perpendicular dissymmetric planes (e.g., certain biphenyls, allenes, and spiro compounds) and can rotate plane-polarized light.

Because asymmetric centers and other chemical structure exist in the compounds of formula I which may give rise to optical isomerism, the invention contemplates optical isomers and mixtures thereof. The compounds of formula I include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure optical isomers, i.e., as individual enantiomers or diastereomers, or as stereoisomer-enriched mixtures. Individual stereoisomers of compounds are prepared by synthesis from optically active starting materials containing the desired chiral centers or by preparation of mixtures of enantiomeric products followed by separation, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of optical isomers that are non-superimposable mirror images of each other.

The term "diastereoisomers" means optical isomers which are not mirror images of each other.

The term "racemic mixture" means a mixture containing equal parts of individual enantiomers.

The term "non-racemic mixture" means a mixture containing unequal parts of individual enantiomers or stereoisomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, cyclic structures, and the like may be present in the compounds of formula I, the invention contemplates each of the various stable geometric isomers and mixtures thereof resulting from the arrangement of substituents around these double bonds and in these cyclic structures. The substituents and the isomers are designated using the cis/trans convention.

Some of the compounds of formula I can exist in more than one tautomeric form. As mentioned above, the compounds of formula I include all such tautomers.

In general, all tautomeric forms and isomeric forms and mixtures thereof, for example, individual geometric isomers, stereoisomers, optical isomers or racemic or non-racemic mixtures of isomers, of a chemical structure or compound is intended, unless the specific stereochemistry or isomeric form is specifically indicated in the compound name or structure.

C. Pharmaceutical Administration and Treatment Terms and Conventions

The term "patient" includes both human and non-human mammals.

The term "therapeutically effective amount" means an amount of a compound according to the invention which, when administered to a patient in need thereof, is sufficient to effect treatment of a hepatitis C viral infection. Such a therapeutically effective amount can be determined routinely by one of ordinary skill in the art having regard to their own knowledge, the prior art, and this disclosure.

The terms "treating" or "treatment" mean the treatment of a hepatitis C viral infection in a patient, and include:

(i) preventing the hepatitis C viral infection from occurring in a patient, in particular, when such patient is predisposed to such disease-state but has not yet been diagnosed as having it;

(ii) inhibiting or ameliorating the hepatitis C viral infection, i.e., arresting or slowing its development; or (iii) relieving the hepatitis C viral infection, i.e., causing regression or cure of the disease-state.

PREFERRED EMBODIMENTS OF THE INVENTION

The preferred embodiment which we refer to herein as the "Lipid-Based System" is directed to a pharmaceutical composition comprising:

(a) a compound of formula (I):

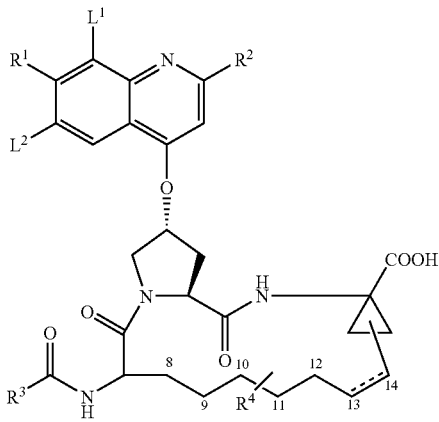

wherein:
—designates an optional bond forming a double bond between positions 13 and 14;
$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
$L^1$, $L^2$ are each independently H, halogen, $C_{1-4}$ alkyl, —O—$C_{1-4}$ alkyl, or —S—$C_{1-4}$ alkyl (the sulfur being in any oxidized state);
$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_6$ or 10 aryl or Het, wherein Het is a five-, six-, or seven-membered saturated or unsaturated heterocycle containing from one to four ring heteroatoms selected from nitrogen, oxygen and sulfur;
said cycloalkyl, aryl or Het being optionally substituted with $R^6$,
wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, $NH—C(O)—R^7$; or $NH—C(O)—NH—R^7$, wherein each $R^7$ is independently: H, $C_{1-6}$ alkyl or $C_{3-6}$ cycloalkyl;
or $R^6$ is $NH—C(O)—OR^8$ wherein $R^8$ is $C_{1-6}$ alkyl or $C_{3-6}$ cycloalkyl;
$R^3$ is $R^9O$— or $R^9NH$—, wherein $R^9$ is $C_{1-6}$ alkyl or $C_{3-6}$ cycloalkyl;
$R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

or a tautomer thereof;

(b) about 0.1 to 10% by weight of a pharmaceutically acceptable amine or a mixture of pharmaceutically acceptable amines;

(c) about 0.1 to 10% by weight of a pharmaceutically acceptable base or a mixture of pharmaceutically acceptable bases;

(d) one or more pharmaceutically acceptable oils;

(e) optionally one or more pharmaceutically acceptable hydrophilic solvents;

(f) optionally one or more pharmaceutically acceptable polymers; and (g) optionally one or more pharmaceutically acceptable surfactants.

The amount of the active ingredient (formula (I) compound) that may be present in the lipid-based system composition may vary widely or be adjusted widely depending on the intended route of administration, the potency of the particular active ingredient being used, the severity of the hepatitis C viral infection and the required concentration. In a particular embodiment, the compound of formula (I) is present in the lipid-based system in an amount of from about 1% to 50% by weight, preferably from about 5% to 30% by weight, more preferably from about 10% to 20% by weight.

Pharmaceutically acceptable amines useful in the composition include, for example, $C_{1-6}$ alkylamine, di-($C_{1-6}$ alkyl)-amine or tri-($C_{1-6}$ alkyl)-amine, wherein one or more alkyl groups thereof may be optionally substituted by one or more hydroxy groups, or $C_{1-6}$ alkylenediamine, a basic amino acid or choline hydroxide, or mixtures thereof. Specific amines include ethanolamine, diethanolamine, triethanolamine, tris (hydroxymethyl)aminomethane, ethylenediamine, dimethylaminoethanol, or meglumine, or mixtures thereof. A preferred amine is tris(hydroxymethyl)aminomethane (also called "Tris" or "Tromethamine"). The amine is present in an amount of about 0.1 to 10% by weight, more preferably in an amount of from about 0.5% to 7% by weight; even more preferably from about 0.5% to 5% by weight.

Pharmaceutically acceptable bases useful in the composition include, for example, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide. Also suitable are bases which are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium. Some preferred bases include sodium hydroxide, potassium hydroxide, sodium hydrogen carbonate, aluminum hydroxide, magnesium hydroxide, magnesium aluminum hydroxide. The pharmaceutically acceptable base is present in the composition in an amount of from about 0.1 to 10% by weight, for example about 0.1 to 5% by weight, for example about 0.1 to 3% by weight.

Pharmaceutically acceptable oils useful in the composition includes a broad spectrum of water-immiscible materials such as, for example, medium or long chain mono-, di- or triglycerides, vegetable oils such as soybean oil, avocado oil, squalene oil, sesame oil, olive oil, canola oil, corn oil, rapeseed oil, safflower oil, and sunflower oil, fish oils, flavored oils, water insoluble vitamins, fatty acids, and mixtures thereof. More preferred oils include mono-, di- or triglycerides of caprylic fatty acids; mono-, di- or triglycerides of capric fatty acids; oleic acid, and mixtures thereof. Some preferred oils include those commercially available under the trade names: CAPMUL®MCM, CAPMUL®MCM C-8, CAPMUL®MCM C-10, CAPMUL®PG-8, MIGLYOL®810, CAPTEX®335, MIGLYOL®812, CAPTEX®200, MYVACET®, MYVEROL®18–92, MAISINE®, and ARLACEL®186. The amount of oil(s) in the composition may vary over a wide range and the optimum amount for a particular composition will depend on the type and amount of other the other ingredients in the composition as can be determined by the skilled pharmaceutical technician. In general, however, the pharmaceutically acceptable oil is present in an amount of from about 1% to 99% by weight, more preferably in an amount of from about 20% to 70% by weight.

In certain circumstances, e.g. for the purpose of increasing solubility, improving dispersability, pharmaceutically acceptable hydrophilic solvents can optionally be used in the composition, which include, for example, propylene glycol, polypropylene glycol, polyethylene glycol (e.g., PEG 400), glycerol, ethanol, dimethyl isosorbide, glycofurol, propylene carbonate, dimethyl acetamide, water, or mixtures thereof; preferably, propylene glycol, polyethylene glycol, ethanol, water, or mixtures thereof. A preferred solvent is a mixture of propylene glycol, ethanol and water. The amount of solvent in the composition may vary over a wide range and the optimum amount for a particular composition will depend on the type and amount of other the other ingredients in the composition as can be easily determined by the skilled worker. In general, however, the solvent(s) are present in an amount of up to about 70% by weight, preferably from about 10% to 30% by weight.

To adjust the viscosity of the formulations or to improve stability, pharmaceutically acceptable polymers can optionally be used in the composition, which include, for example, polyethylene glycols (e.g., PEG 1000, PEG 1500, PEG 3350, PEG 6000 and PEG 8000), polyvinylpyrrolidones (e.g., KOLLIDON®12 PF, KOLLIDON®17 PF, KOLLIDON®25 PF, KOLLIDON®30 PF, KOLLIDON®90 PF etc.), polyvinylalcohols, cellulose derivatives (e.g., hydroxypropylmethylcellulose (HPMC), hydroxypropylcellulose (HPC)), polyacrylates, polymethacrylates, sugars (e.g., lactose), polyols, and mixtures thereof. When used in the composition, the pharmaceutically acceptable polymer is preferably be present in an amount up to about 50% by weight, preferably about 1 to 20% by weight.

To facilitate self-emulsification, pharmaceutically acceptable surfactants can optionally be used in the composition, which include, for example, vitamin derivatives such as Vitamin E TPGS (d-alpha tocopheryl polyethylene glycol 1000 succinate), polyoxyl castor oils (e.g., CREMOPHOR®EL), polyoxyl hydrogenated castor oils, polysorbates (e.g., TWEEN®80), peglicol 6-oleate, polyoxyethylene stearates, polyglycolyzed glycerides (e.g., GELUCIRE®44/14) or poloxamers (e.g., PLURONIC® F68), sodium lauryl sulfate and mixtures thereof. Preferred surfactants include Vitamin E TPGS, polyoxyl 40 hydrogenated castor oil or polyoxyl 35 castor oil, and mixtures thereof.

When used in the composition, the surfactant is preferably present in an amount of up to about 70% by weight, preferably from about 20% to 50% by weight. This type of lipid-based system of the present invention further incorporating a surfactant is generally referred to herein as "self-emulsifying drug delivery system" or "SEDDS".

A particular embodiment of the SEDDS composition according to the present invention is directed to a pharmaceutical composition, comprising:
  (a) about 5% to 30% by weight of a compound of formula (I);
  (b) about 0.1% to 7% by weight of a pharmaceutically acceptable amine;
  (c) about 0.1% to 5% by weight of a pharmaceutically acceptable base;
  (d) about 1% to 99% by weight of a pharmaceutically acceptable oil;
  (e) up to about 70% by weight of a pharmaceutically acceptable hydrophilic solvent;
  (f) optionally up to about 50% by weight of a pharmaceutically acceptable polymer; and
  (g) up to about 70% by weight of a pharmaceutically acceptable surfactant.

A further particular embodiment of the SEDDS composition according to the present invention is directed to a pharmaceutical composition, comprising:
  (a) about 10% to 20% by weight of a compound of formula (I);
  (b) about 0.1% to 5% by weight of a pharmaceutically acceptable amine;
  (c) about 0.1% to 3% by weight of a pharmaceutically acceptable base;
  (d) about 20% to 70% by weight of a pharmaceutically acceptable oil;
  (e) about 10% to 30% by weight of a pharmaceutically acceptable hydrophilic solvent;
  (f) optionally about 1% to 20% by weight of a pharmaceutically acceptable polymer; and
  (g) about 20% to 50% by weight of a pharmaceutically acceptable surfactant.

A further particular embodiment of the SEDDS composition according to the present invention is directed to a pharmaceutical composition, comprising:
  (a) about 10% to 20% by weight of a compound of formula (I);
  (b) about 0.1% to 5% by weight of tris(hydroxymethyl) aminomethane;
  (c) about 0.1% to 3% by weight of sodium hydroxide;
  (d) about 20% to 70% by weight of a triglyceride of caprylic fatty acid or a triglyceride of capric fatty acid, or mixtures thereof;
  (e) about 10% to 30% by weight of a mixture of propylene glycol, ethanol and optionally water;
  (f) optionally about 1% to 20% by weight of polyethylene glycol or polyvinylpyrrolidone; and
  (g) about 20% to 50% by weight of d-alpha tocopheryl polyethylene glycol 1000 succinate or polyoxyl 35 castor oil.

A further particular embodiment of the SEDDS composition according to the present invention is directed to a pharmaceutical composition, comprising:
  (a) about 10% to 15% by weight of a compound of formula (I);
  (b) about 0.1% to 2% by weight of tris(hydroxymethyl) aminomethane;
  (c) about 0.1% to 1% by weight of sodium hydroxide;
  (d) about 20% to 30% by weight of medium chain mono-and diglycerides or medium chain triglyceride;
  (e) about 15% to 25% by weight of a mixture of propylene glycol, ethanol and water; and (f) about 40% to 50% by weight of d-alpha tocopheryl polyethylene glycol 1000 succinate; and (g) about 0.01% to 1% of dl-α-tocopherol.

The Lipid-Based System composition may be prepared in a conventional manner, for example, by a method comprising: mixing together the liquid components, e.g., the pharmaceutically acceptable oil(s), and any surfactant(s) and solvent(s); dissolving the pharmaceutically acceptable amine(s), base(s) and polymer(s) in the resulting mixture; optionally heating the mixture obtained if necessary to sufficiently melt one or more of the components of the mixture; adding the compound of formula (I) to the resulting mixture and further mixing until all or substantially all of the compound of formula I is solubilized. This method of preparing the composition constitutes another aspect of the present invention. The resulting solution is then optionally formulated into the desired dosage form, for example, capsules, including hard shell or softgel capsules (e.g., hard or soft gelatin capsules), by known manufacturing technology. The composition may also be in the form of a liquid solution or semi-solid for oral, parenteral, rectal or topical administration. Examples of soft gelatin capsules that can be used include those disclosed in EP 649651 B1 and U.S. Pat. No. 5,985,321.

Optional Additional Ingredients

If desired, the compositions according to the present invention may further include conventional pharmaceutical additives as is necessary or desirable to obtain a suitable formulation, such as antioxidants, lubricants, disintegrants, preservatives, buffers, stabilizers, thickening agents, coloring agents, flavoring agents, fragrances, etc. Additional additives that may be useful in the compositions of the invention are disclosed in Tsantrizos et al.

In one preferred embodiment, the compositions according to the present invention further contain one or more antioxidants. Preferred antioxidants include, for example, ascorbic acid, sulfatide salts, citric acid, propyl gallate, dl-α-tocopherol, ascorbyl palmitate, BHT or BHA. If present, the antioxidant is generally present in an amount of from about 0.01% to 1% by weight.

Compounds of Formula (I)

Preferred embodiments for the compounds of formula (I) in the compositions are as set forth below.

Preferred embodiments include compounds of formula I as described above, wherein the cyclopropyl moiety is selected from the 2 different diastereoisomers where the 1-carbon center of the cyclopropyl has the R configuration as represented by structures (i) and (ii):

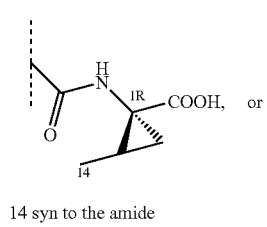

14 syn to the amide

-continued

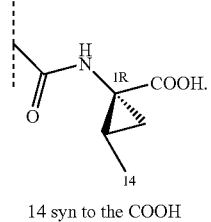

14 syn to the COOH

More preferably, position 14 is linked to cyclopropyl group in the configuration syn to the COOH group as represented by structure (ii).

Thus, in one embodiment, in the compound of formula (I) the following moiety:

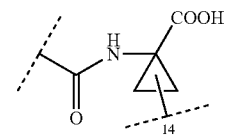

has the configuration represented by the following diastereoisomer:

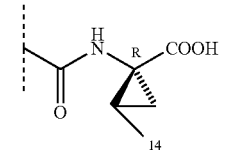

in which configuration position 14 is linked syn to the COOH group.

In another embodiment, in the compound of formula (I):
$R^1$ is H, $C_{1-6}$ alkyl, $C_{1-6}$ alkoxy, hydroxy, chloro, or $N(R^5)_2$, wherein $R^5$ is H or $C_{1-6}$ alkyl;
$L^1$ and $L^2$ are each H; and
$R^2$ is H, $C_{1-6}$ thioalkyl, $C_{1-6}$ alkoxy, phenyl or Het selected from the following:

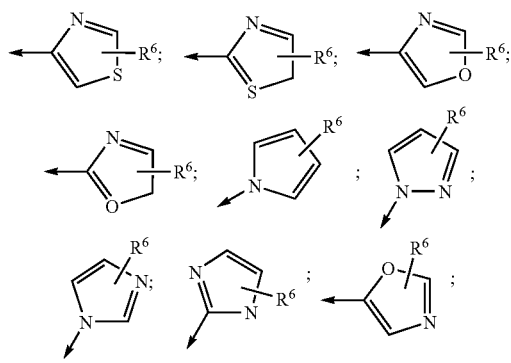

-continued

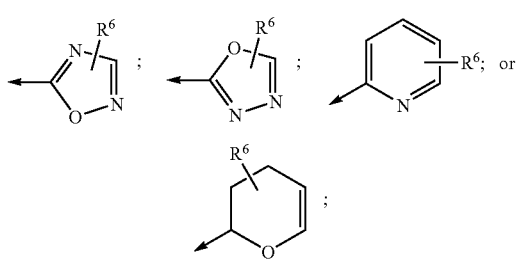

wherein R⁶ is H, $C_{1-6}$ alkyl, NH—R⁷, NH—C(O)—R⁷, NH—C(O)—NH—R⁷, wherein each R⁷ is independently: H, $C_{1-6}$ alkyl, or $C_{3-6}$ cycloalkyl;

or NH—C(O)—OR⁸, wherein R⁸ is $C_{1-6}$ alkyl.

In another embodiment, in the compounds of formula (I):
L¹ and L² are each H.

In another embodiment, in the compound of formula (I):
R¹ is H or $C_{1-6}$alkoxy.

In another embodiment, in the compound of formula (I):
R² is $C_{1-4}$ alkoxy, phenyl or Het selected from the following groups:

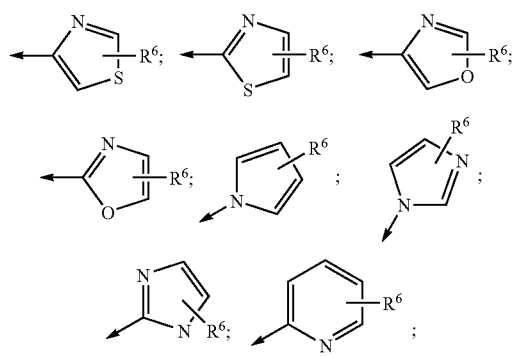

wherein R⁶ is H, $C_{1-6}$ alkyl, NH—R⁷, or NH—C(O)—R⁷;
wherein each R⁷ is H, $C_{1-6}$ alkyl or $C_{3-6}$ cycloalkyl, or NH—C(O)—OR⁸, wherein R⁸ is $C_{1-6}$ alkyl.

In another embodiment, in the compound of formula (I):
R² is ethoxy, or Het selected from the following groups:

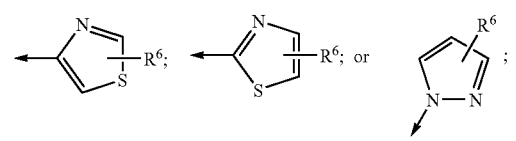

wherein R⁶ is NHR⁷ or NH—C(O)—R⁷, wherein R⁷ is H, $C_{1-6}$ alkyl or $C_{3-6}$ cycloalkyl;
or R⁶ is NH—C(O)—OR⁸, wherein R⁸ is $C_{1-6}$ alkyl.

In another embodiment, in the compound of formula (I):
R² is selected from the following groups:

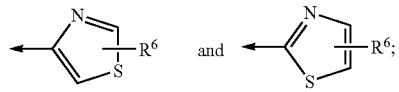

R⁶ is NHR⁷, wherein each R⁷ is independently: H, $C_{1-6}$ alkyl, or $C_{3-6}$ cycloalkyl.

In another embodiment, in the compound of formula (I):
R³ is R⁹O—, wherein R⁹ is butyl, cyclobutyl or cyclopentyl.

In another embodiment, in the compound of formula (I):
the bond at position 13–14 is a single bond.

In another embodiment, in the compound of formula (I):
the bond at position 13–14 is a double bond and said double bond is cis.

In another embodiment, in the compound of formula (I):
R⁴ is H or $C_{1-6}$ alkyl.

In another embodiment, in the compound of formula (I):
R¹ is methoxy;
L¹ and L² are each H;
R² is

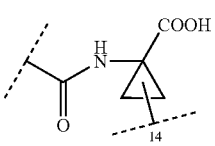

wherein R⁶ is NH—($C_{1-4}$alkyl) or NH—($C_{3-6}$cycloalkyl);
R³ is R⁹O—, wherein R⁹ is butyl, cyclobutyl or cyclopentyl;
R⁴ is H or $C_{1-6}$ alkyl;
and following moiety:

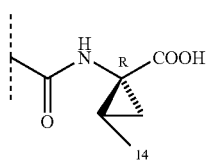

has the configuration represented by the following diastereoisomer:

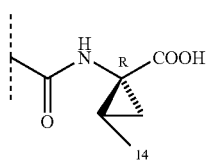

in which configuration position 14 is linked syn to the COOH group.

Tables of Compounds

The following tables list compounds representative of the compounds of formula (I).

TABLE 1
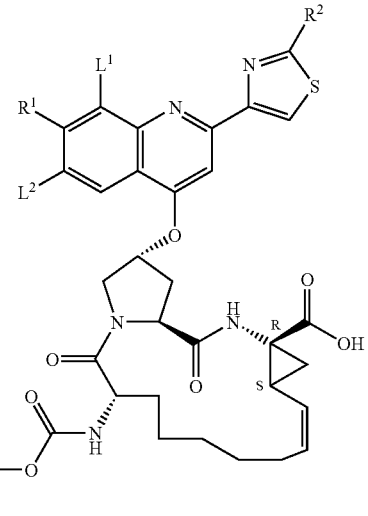
| Cpd # | L² | R¹ | L¹ | R² | MS (M + H)+ |
|---|---|---|---|---|---|
| 101 | H | —OMe | Me | 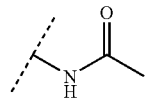 | 789.4 |
| 102 | H | —OMe | Me | 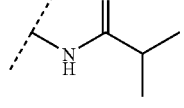 | 789.3 |
| 103 | H | —OMe | Me | 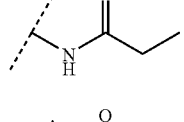 | 817.4 |
| 104 | H | —OMe | Me | 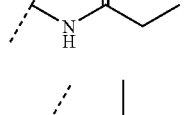 | 803.4 |
| 105 | H | —OMe | Br | 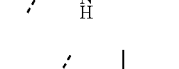 | 867.3 869.3 |
| 106 | H | —OMe | Br |  | 853.3 855.3 |
| 107 | H | —OMe | Cl | 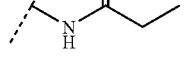 | 809.3 811.3 |
| 108 | H | —OMe | Cl | 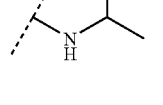 | 823.3 825.3 |
| 109 | Me | —OMe | Me | 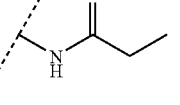 | 803.4 |
TABLE 1-continued
| Cpd # | L² | R¹ | L¹ | R² | MS (M + H)+ |
|---|---|---|---|---|---|
| 110 | Me | —OMe | Me | 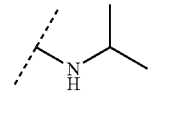 | 817.4 |
| 111 | H | —OMe | F | 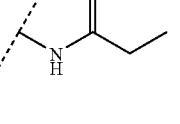 | 793.4 |
| 112 | H | —OMe | F | 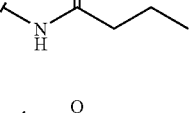 | 807.3 |
| 113 | H | —OMe | Cl | 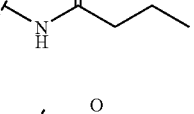 | 837.3 839.2 |
| 114 | H | —OMe | Br | 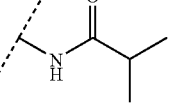 | 881.2 883.2 |
| 115 | H | —OMe | Br | 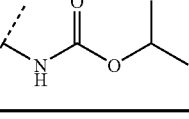 | 881.2 883.2 |
| 116 | H | —OMe | Br |  | 897.2 899.2 |

TABLE 2

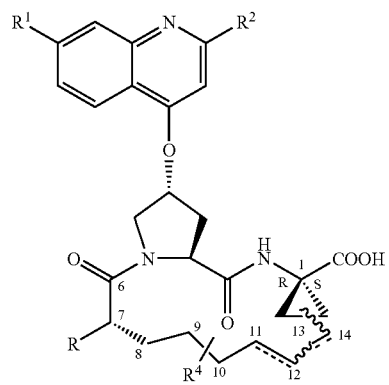

directed to a single stereoisomer at the cyclopropyl moiety, wherein R, R⁴, said double bond position, cyclopropyl group to 14-position bond stereochemistry, and $R^1$ and $R^2$ are defined as follows:

| Cpd # | R: | R⁴: | double bond: | cyclopropyl to 14-position bond stereochemistry: | R¹: | R²: |
|---|---|---|---|---|---|---|
| 205 | NH-Boc | 11-OH 12-OH cis | none | 1R or 1S, 14 is syn to acid | H | H; |
| 206 | NH-Boc | H | 13,14-cis | 1R, 14 is syn to acid | H | H; |
| 207 | NH-Boc | H | 13,14-cis | 1R, 14 is syn to acid | OMe | H; |
| 208 | NH-Boc | H | 13,14-cis | 1R, 14 is syn to acid | OMe | phenyl; |
| 209 | NH—C(O)—NH-tBu | H | 13,14-cis | 1R, 14 is syn to acid | OMe | phenyl; |
| 210 | NH-Boc | H | 13,14-cis | 1S, 14 is syn to acid | OMe | phenyl; |
| 214 | NH-Boc | 10-oxo | 13,14-cis | 1R, 14 is syn to acid | OMe | phenyl; |
| 215 | NH-Boc | H | none | 1R, 14 is syn to acid | OMe | phenyl; |
| 217 | NH-Boc | 10-OH (mixt dia stereo) | 13,14-cis | 1R, 14 is syn to acid | OMe | phenyl; |
| 218 | NH-Boc | 10-oxo | 13,14-cis | 1R, 14 is syn to amide | OMe | phenyl; |
| And 220 | NH-Boc | H | 13,14-cis | 1R, 14 is syn to amide | OMe | thiazol-2-yl. |

TABLE 3

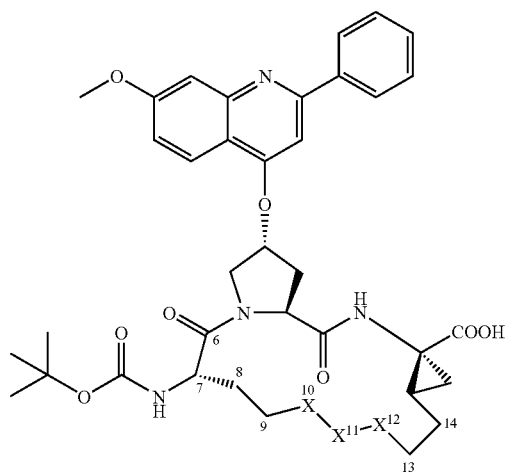

wherein the bond from position 14 to the cyclopropyl group is syn to the COOH, $X_{10}$, $X_{11}$, and $X_{12}$ are defined as follows:

| Cpd # | $X_{10}$: | $X_{11}$: | $X_{12}$: |
|---|---|---|---|
| 502 | $CH_2$ | $CH_2$ | $CH_2$. |

TABLE 4

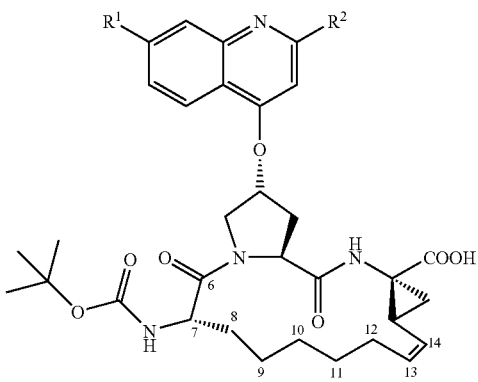

wherein the bond from position 14 to the cyclopropyl group is syn to the COOH, and R¹ and R² are defined as follows:

| Cpd # | R¹: | R²: |
|---|---|---|
| 601 | N(Me)₂ | (thiazol-4-yl with 2-NHC(O)CH₃) |
| 602 | OH | (CF₃) |
| and 603 | OMe | (oxazol-5-yl) |

TABLE 5

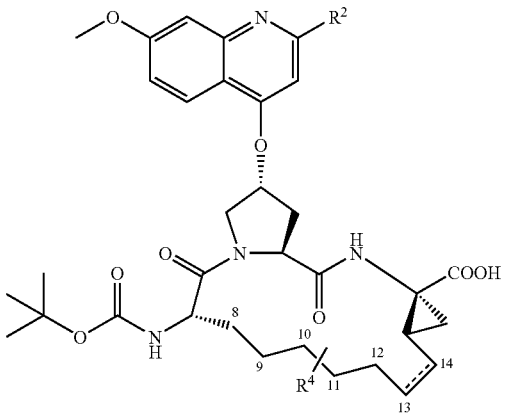

wherein the bond from position 14 to the cyclopropyl group is syn to the COOH, and R⁴, the 13, 14 double bond and R² are defined as follows:

| Cpd # | R⁴: | 13, 14 double bond: | R²: |
|---|---|---|---|
| 702 | H | Cis | (thiazol-4-yl with 2-NHC(O)CH₃) |

TABLE 5-continued

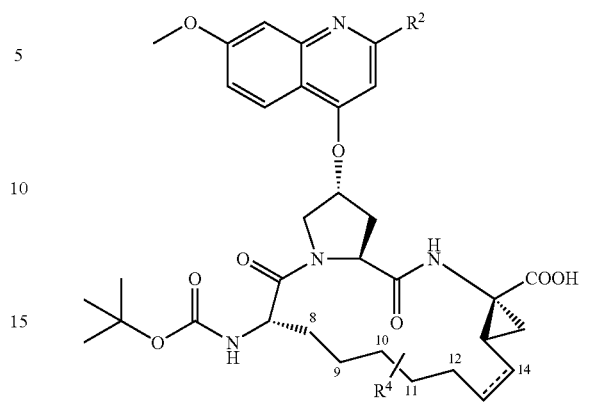

wherein the bond from position 14 to the cyclopropyl group is syn to the COOH, and R⁴, the 13, 14 double bond and R² are defined as follows:

| Cpd # | R⁴: | 13, 14 double bond: | R²: |
|---|---|---|---|
| 703 | H | None | (thiazol-4-yl with 2-NHEt) |
| 704 | H | Cis | (pyridin-2-yl) |
| 705 | H | Cis | (thiazol-2-yl) |
| 707 | H | Cis | (thiazol-4-yl with 2-iPr) |
| 708 | H | Cis | (thiazol-4-yl with 2-NHEt) |
| 709 | H | None | (thiazol-4-yl with 2-NHC(O)CH₃) |
| 710 | H | None | (thiazol-4-yl with 2-iPr) |
| 711 | H | None | (pyridin-2-yl) |
| 712 | H | Cis | —OEt; |

TABLE 5-continued

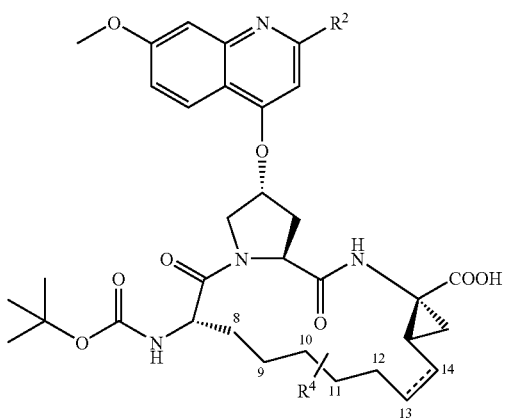

wherein the bond from position 14 to the cyclopropyl group is syn to the COOH, and R⁴, the 13, 14 double bond and R² are defined as follows:

| Cpd # | R⁴: | 13, 14 double bond: | R²: |
|---|---|---|---|
| 713 | H | None | thiazol-2-yl |
| 714 | H | None | —OEt |
| 715 | H | Cis | pyrrol-1-yl |
| 716 | H | Cis | 1,3,4-oxadiazol-2-yl |
| 717 | H | Cis | 1,3,4-oxadiazol-3-yl |
| 718 | H | Cis | imidazol-1-yl |
| 719 | H | Cis | 6-methylpyridin-2-yl |
| 720 | H | None | 4-(NHC(O)H)-thiazol-2-yl |

TABLE 5-continued

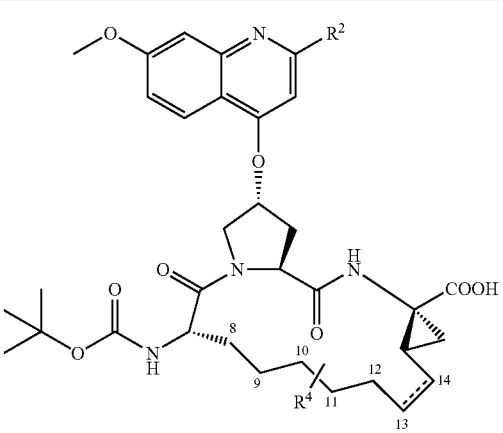

wherein the bond from position 14 to the cyclopropyl group is syn to the COOH, and R⁴, the 13, 14 double bond and R² are defined as follows:

| Cpd # | R⁴: | 13, 14 double bond: | R²: |
|---|---|---|---|
| 721 | H | None | 6-methylpyridin-2-yl |
| 722 | H | Cis | 4-methylimidazol-1-yl |
| 723 | H | None | pyrrol-1-yl |
| 724 | H | None | 4-(NHC(O)OMe)-thiazol-2-yl |
| 725 | H | Cis | 4-isopropylthiazol-2-yl |
| 726 | H | Cis | 1-methylimidazol-2-yl |

TABLE 5-continued

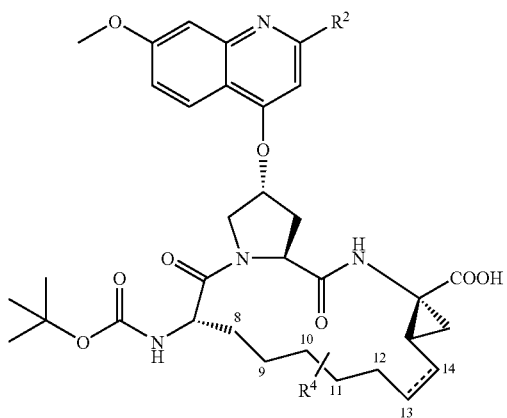

wherein the bond from position 14 to the cyclopropyl group is syn to the COOH, and R⁴, the 13, 14 double bond and R² are defined as follows:

| Cpd # | R⁴: | 13, 14 double bond: | R²: |
|---|---|---|---|
| 727 | H | Cis | —CH₂—OMe; |
| 728 | H | Cis | Me; |
| 729 | H | Cis | 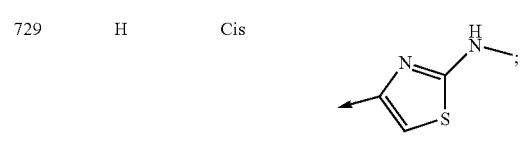 |
| 730 | H | None | 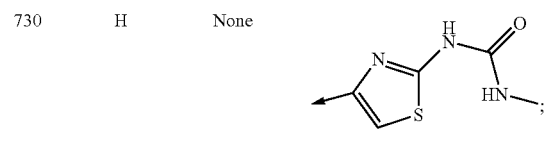 |
| 731 | H | Cis |  |
| 732 | H | Cis |  |
| 733 | H | Cis | 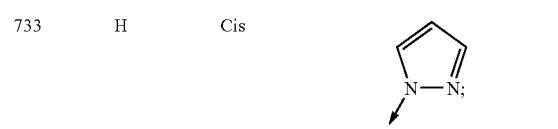 |
| 734 | H | Cis | 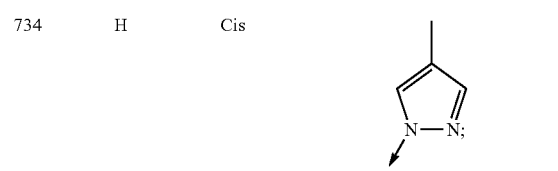 |
| 735 | H | Cis | 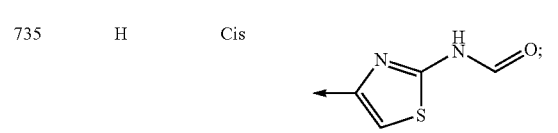 |

TABLE 5-continued

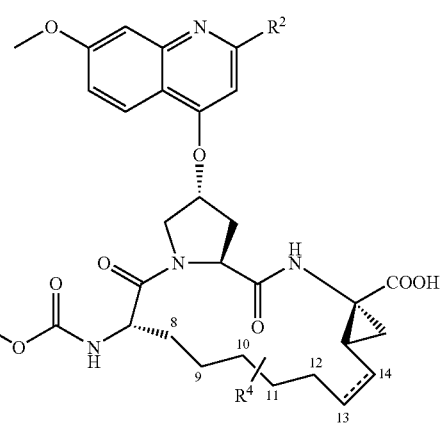

wherein the bond from position 14 to the cyclopropyl group is syn to the COOH, and R⁴, the 13, 14 double bond and R² are defined as follows:

| Cpd # | R⁴: | 13, 14 double bond: | R²: |
|---|---|---|---|
| 736 | H | Cis | 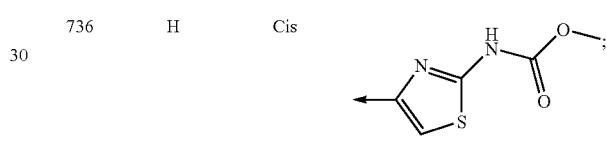 |
| 737 | H | Cis | 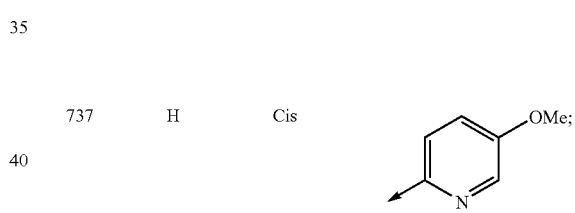 |
| 738 | H | Cis |  |
| 739 | 10-(R) Me | none | Ph; |
| 740 | 10-(S) Me | none | Ph; |
| and 741 | H | Cis |  |

TABLE 6

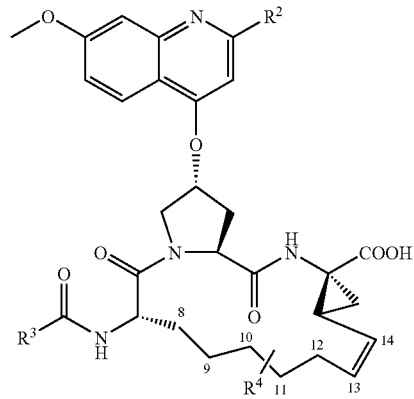

wherein the bond from position 14 to the cyclopropyl group is syn to the COOH, said 13, 14 double bond is cis, $R^3$, $R^4$ and $R^2$ are defined as follows:

| Cpd # | $R^3$: | $R^4$: | $R^2$: |
|---|---|---|---|
| 801 | cyclobutyl-O- | H | 2-(acetylamino)thiazol-4-yl |
| 804 | (S)-3,3-dimethylbutan-2-ylamino- | H | 2-(acetylamino)thiazol-4-yl |
| 805 | cyclopentyl-O- | H | pyrrol-1-yl |
| 807 | cyclopentyl-O- | H | OEt; |
| 808 | isopropyl-O- | H | OEt; |
| 809 | cyclopentyl-O- | H | 2-(acetylamino)thiazol-4-yl |
| 810 | cyclopentyl-O- | H | 2-(ethylamino)thiazol-4-yl |
| 811 | cyclopentyl-O- | H | 2-(methylamino)thiazol-4-yl |
| 812 | cyclopentyl-O- | H | 2-aminothiazol-4-yl |

TABLE 6-continued

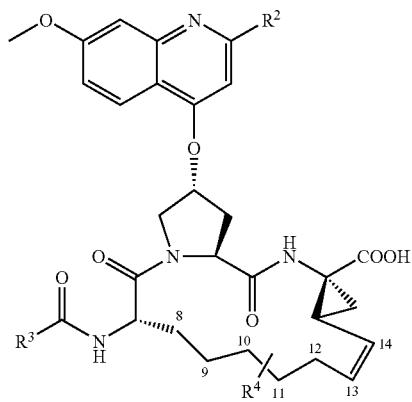

wherein the bond from position 14 to the cyclopropyl group is syn to the COOH, said 13, 14 double bond is cis, $R^3$, $R^4$ and $R^2$ are defined as follows:

| Cpd # | $R^3$: | $R^4$: | $R^2$: |
|---|---|---|---|
| 814 | cyclopentyl-O- | H | 2-thiazolyl |
| 815 | cyclopentyl-O- | H | 2-pyridyl |
| 816 | t-Bu-CH(CH₃)-NH- | H | 2-(ethylamino)thiazol-4-yl |
| 817 | cyclopentyl-O- | H | 4-isopropylthiazol-2-yl |
| 818 | cyclopentyl-O- | H | 2-(methoxycarbonylamino)thiazol-4-yl |
| 819 | cyclopentyl-O- | H | 2-(isobutoxycarbonylamino)thiazol-4-yl |

TABLE 6-continued

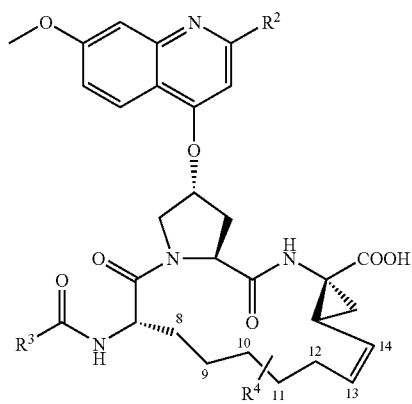

wherein the bond from position 14 to the cyclopropyl group is syn to the COOH, said 13, 14 double bond is cis, $R^3$, $R^4$ and $R^2$ are defined as follows:

| Cpd # | $R^3$: | $R^4$: | $R^2$: |
| --- | --- | --- | --- |
| 820 | cyclobutyl-O- | H | thiazol-4-yl-2-NHEt; |
| 821 | cyclopentyl-O- | H | pyrazol-1-yl; |
| 822 | cyclopentyl-O- | H | thiazol-4-yl-2-NHiPr; |
| 823 | cyclopentyl-O- | H | pyrazol-1-yl; |
| 824 | cyclopentyl-O- | 10-(R) Me | OEt; |
| 825 | cyclopentyl-O- | H | thiazol-4-yl-2-NHcyclopropyl; |
| 826 | cyclopentyl-O- | H | thiazol-4-yl-2-NHcyclobutyl; |
| 827 | cyclopentyl-O- | H | thiazol-4-yl-2-NHcyclopentyl; |

TABLE 6-continued

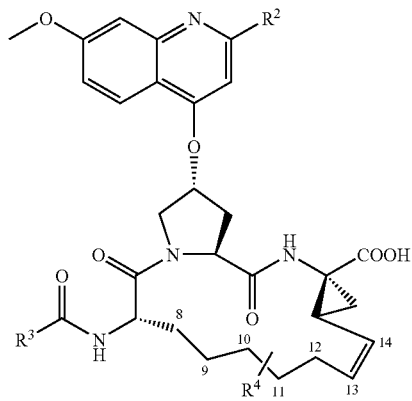

wherein the bond from position 14 to the cyclopropyl group is syn to the COOH, said 13, 14 double bond is cis, R³, R⁴ and R² are defined as follows:

| Cpd # | R³: | R⁴: | R²: |
|---|---|---|---|
| and 828 | cyclopentyl-O- | H | 2-(cyclohexylamino)thiazol-4-yl |

TABLE 7

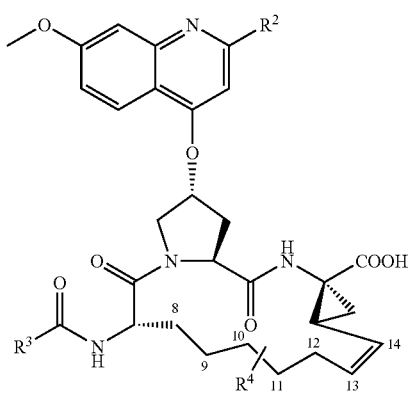

wherein the bond from position 14 to the cyclopropyl group is syn to the COOH, and R³, R⁴ and R² are defined as follows:

| Cpd # | R³: | R⁴: | R²: |
|---|---|---|---|
| 901 | cyclopentyl-O- | H | OEt; |
| 902 | cyclopentyl-O- | H | thiazol-2-yl; |
| 903 | cyclobutyl-O- | H | thiazol-2-yl; |

TABLE 7-continued

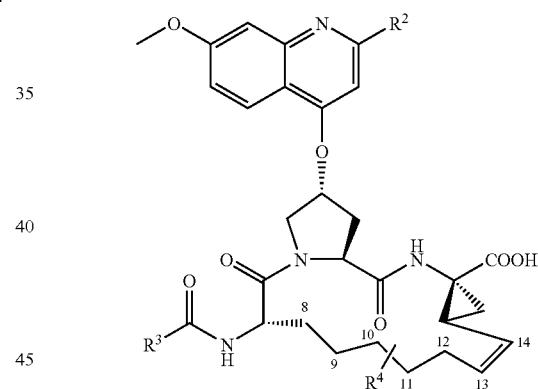

wherein the bond from position 14 to the cyclopropyl group is syn to the COOH, and R³, R⁴ and R² are defined as follows:

| Cpd # | R³: | R⁴: | R²: |
|---|---|---|---|
| 904 | cyclopentyl-O- | H | pyrazol-1-yl; |
| 905 | cyclobutyl-O- | H | pyrazol-1-yl; |
| 906 | cyclopentyl-O- | H | 4-isopropylthiazol-2-yl; |

TABLE 7-continued

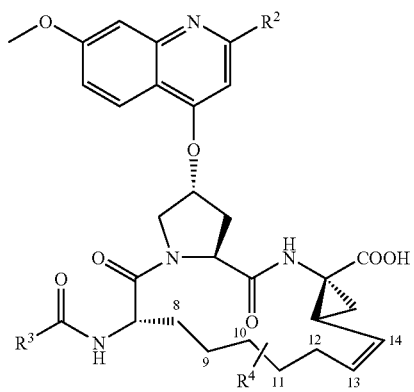

wherein the bond from position 14 to the cyclopropyl group is syn to the COOH, and R³, R⁴ and R² are defined as follows:

| Cpd # | R³: | R⁴: | R²: |
|---|---|---|---|
| 907 | cyclopentyl-O- | H | pyrrolyl |
| 908 | cyclopentyl-O- | H | 2-amino-thiazolyl |
| 909 | cyclopentyl-O- | H | 2-acetamido-thiazolyl |
| 910 | cyclopentyl-O- | H | 2-ethylamino-thiazolyl |
| 911 | cyclopentyl-O- | H | 2-isopropylamino-thiazolyl |
| 912 | cyclobutyl-O- | H | 2-ethylamino-thiazolyl |
| 913 | cyclobutyl-O- | H | 2-acetamido-thiazolyl |
| 914 | cyclopentyl-O- | H | 2-methylamino-thiazolyl |

TABLE 7-continued

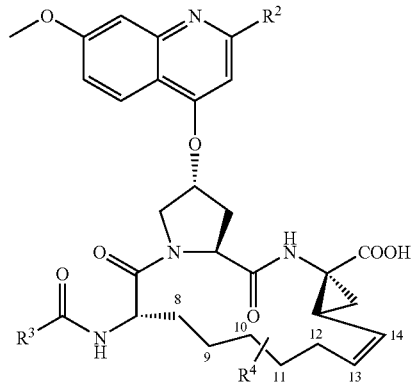

wherein the bond from position 14 to the cyclopropyl group is syn to the COOH, and R³, R⁴ and R² are defined as follows:

| Cpd # | R³: | R⁴: | R²: |
|---|---|---|---|
| 915 | isobutyl-O- | H | 2-ethylamino-thiazolyl |
| and 916 | cyclopentyl-O- | 10(R) Me | OEt. |

A preferred compound of formula (I) for the compositions of the invention described herein is Compound #822. Additional specific compounds that are representative of the compounds of formula (I) may be found in Tsantrizos et al. and WO 00/59929.

The compounds of formula I may be synthesized by the procedures fully set forth in Tsantrizos et al.; WO 00/59929; and Llinas-Brunet.

Methods of Therapeutic Use

The compounds of formula I are effective as HCV protease inhibitors, and these compounds and pharmaceutical compositions comprising these compounds are therefore useful in inhibiting the replication of HCV and in the treatment of HCV infections, as set forth in Tsantrizos et al.; WO 00/59929 and Llinas-Brunet.

As discussed above, the pharmaceutical compositions of the present invention may be formulated into a variety of dosage forms depending upon the particular composition contemplated. Likewise, a variety of modes of administration are possible depending upon the particular composition and dosage form, although oral administration by tablet, capsule or suspension are the preferred modes of administration.

Dosage levels of the compounds of formula (I) and various treatment regimens in the monotherapy for the prevention and treatment of HCV infection are as set forth in Tsantrizos et al.; WO 00/59929 and Llinas-Brunet. As the skilled artisan will appreciate, however, lower dosages may be possible with the compositions of the present invention depending on the level of improvement in bioavailability. Combination therapy is also possible with one or more additional therapeutic or prophylactic agents as fully described by Tsantrizos et al.; WO 00/59929 and Llinas-Brunet. The additional agent(s) may be combined with the compounds of this invention to create a single dosage form or, alternatively, these additional agent(s) may be separately administered to a mammal as part of a multiple dosage form.

In order that this invention be more fully understood, the following examples of are set forth. These examples are for the purpose of illustrating embodiments of this invention, and are not to be construed as limiting the scope of the invention in any way.

EXAMPLES

Formulation #1 comparative)

| Ingredient | Weight (mg/g) | % (w/w) |
|---|---|---|
| Compound #822 | 100 | 10 |
| Tromethamine | 10 | 1 |
| Water | 20 | 2 |
| Ethanol | 100 | 10 |
| Propylene glycol | 50 | 5 |
| Alpha-Tocopherol | 4 | 0.4 |
| Capmul MCM | 220 | 22 |
| $V_E$ TPGS | 516 | 49.6 |

Formulation #2

| Ingredient | Weight (mg/g) | % (w/w) |
|---|---|---|
| Compound #822 | 100 | 10 |
| Tromethamine | 10 | 1 |
| Sodium hydroxide | 3 | 0.3 |
| Water | 17 | 1.7 |
| Ethanol | 100 | 10 |
| Propylene glycol | 50 | 5 |
| Alpha-Tocopherol | 4 | 0.4 |
| Capmul MCM | 220 | 22 |
| $V_E$ TPGS | 516 | 49.6 |

Formulation #3

| Ingredient | Weight (mg/g) | % (w/w) |
|---|---|---|
| Compound #822 | 100 | 10 |
| Tromethamine | 10 | 1 |
| Sodium hydroxide | 3 | 0.3 |
| Water | 30 | 3 |
| Ethanol | 100 | 10 |
| Propylene glycol | 50 | 5 |
| Alpha-Tocopherol | 4 | 0.4 |
| Captex 355 | 220 | 22 |
| $V_E$ TPGS | 483 | 48.3 |

Preparation of Formulations 1–3:

First, the liquid components such as CAPMUL®MCM, CAPTEX®355, propylene glycol, alpha-tocopherol, water and ethanol were mixed together in a tightly closed container. $V_E$ TPGS was melted at 40° C. and then transferred into the container. And then tromethamine and/or sodium hydroxide solution was added to the above mixture. Finally, Compound #822 was added to the container and stirring was continued at 40° C. until the drug was completely solubilized. These formulations can be filled into hard shell or soft gelatin capsules.

Chemical Stability Studies

The major degradation products of compound #822 in the formulation were identified and characterized by LC/MS. To compare different formulations, accelerated stability study was conducted: formulations were sealed into amber ampules and stored at different temperatures: 50, 60 and 70° C. Samples were pulled and analyzed by HPLC for assay and impurity.

Figure 2:
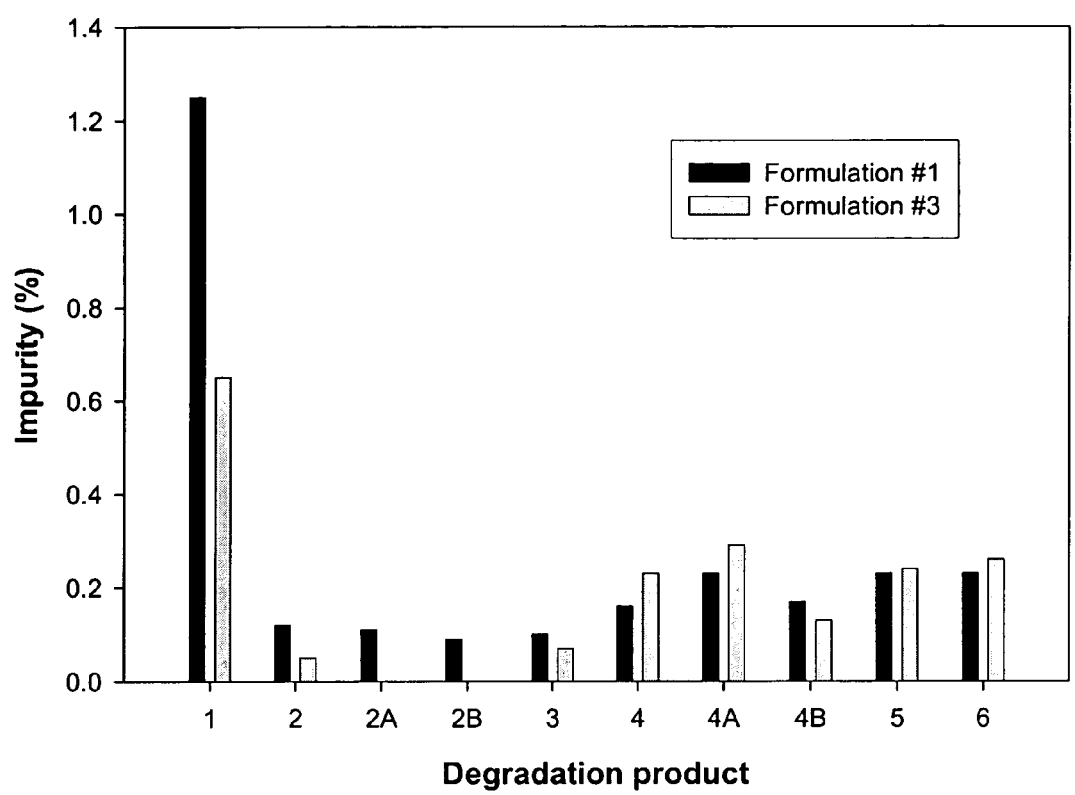
FIG. 2 shows the impurity profile of a second formulation according to the present invention containing tromethamine and sodium (Formulation #3) and a comparative formulation without sodium hydroxide (Formulation #1) when both formulations were subjected to stability testing for 5 days at 70° C. This figure shows that the level of major degration product 1 is lower in Formulation #3 than in comparative Formulation #1.

FIGS. 1 and 2 are impurity profiles of formulations containing compound #822, based on data obtained during an initial study. All formulations were analyzed after 5 days at 70° C. As can be seen in FIGS. 1 and 2, the level of the major degradation product 1 is lower in Formulations #2 and #3 of the invention than in comparative Formulation #1 (without base).

A more comprehensive follow-up study was conducted on Formulations #1 and #3 (the formulations used in this follow-up study were from a different lot and therefore exhibit slightly different levels of impurities vs. the formulations used in the initial study). Both total impurity and the level of major degradation product 1 have been significantly decreased with Formulation #3 compared to Formulation #1. Tables 1a and 1b summarize the amounts of total impurity and major degradation product 1 in Formulation #3 versus comparative Formulation #1 upon storage at different temperatures. It is clear that Formulation #3 is more stable than Formulation #1, having a lower level of both total impurity and major degradation product 1 upon storage. According to Arrhenius equation, $t_{0.1,\ 25}$ (time for degradation product 1 to reach 0.1% at 25° C.) of Formulation #3 is 232 days as compared to 99 days for Formulation #1.

TABLE 1a

Summary of Total Impurity in Formulations #1 and #3.

| Time | Formulation #1 (%) | | | Formulation #3 (%) | | |
|---|---|---|---|---|---|---|
| (day) | 70° C. | 60° C. | 50° C. | 70° C. | 60° C. | 50° C. |
| 1 | 1.51 | | | 1.05 | | |
| 3 | 2.12 | 1.82 | | 1.56 | 1.28 | |
| 5 | 2.91 | | | 2.12 | | |
| 7 | 4.07 | 3.34 | 1.19 | 2.94 | 2.49 | 1.02 |
| 15 | 7.37 | 6.5 | | 5.25 | 4.78 | 1.44 |
| 22 | 10.39 | 7.92 | | 7.51 | 6.37 | |
| 28 | 12.02 | 10.04 | 2.95 | 9.96 | 7.44 | 2.25 |
| 42 | | | 4.48 | | | 3.61 |
| 56 | | | 5.7 | | | 4.15 |

TABLE 1b

Summary of Major Degradation Product 1 in Formulations #1 and #3.

| Time | Formulation #1 (%) | | | Formulation #3 (%) | | |
|---|---|---|---|---|---|---|
| (day) | 70° C. | 60° C. | 50° C. | 70° C. | 60° C. | 50° C. |
| 1 | 0.37 | | | 0.15 | | |
| 3 | 0.66 | 0.48 | | 0.29 | 0.23 | |
| 5 | 1.01 | | | 0.47 | | |
| 7 | 1.43 | 1.15 | 0.26 | 0.68 | 0.55 | 0.13 |
| 15 | 2.9 | 2.46 | | 1.44 | 1.21 | 0.25 |
| 22 | 4.21 | 3.15 | | 2.23 | 1.68 | |
| 28 | 5.32 | 3.9 | 0.96 | 3.08 | 2.1 | 0.5 |
| 42 | | | 1.55 | | | 0.81 |
| 56 | | | 2.09 | | | 1.07 |

What is claimed is:

1. A pharmaceutical composition comprising:
(a) a compound of formula (I):

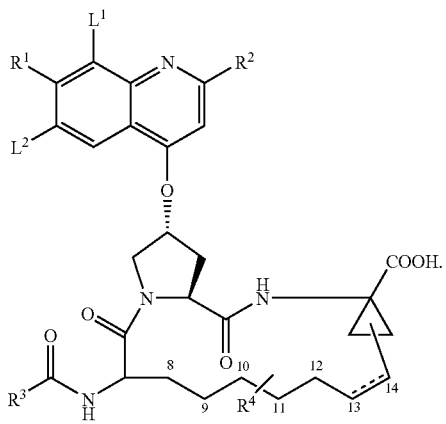

wherein:
----- designates an optional bond forming a double bond between positions 13 and 14;
$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
$L^1$, $L^2$ are each H;
$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\,or\,10}$ aryl or Het, wherein Het is a five-, six-, or seven-membered saturated or unsaturated heterocycle containing from one to four ring heteroatoms selected from nitrogen, oxygen and sulfur;
said cycloalkyl, aryl or Het being optionally substituted with $R^6$,
wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;
or $R^6$ is NH—C(O)—$OR^8$ wherein $R^8$ is $C_{1-6}$ alkyl or $C_{3-6}$ cycloalkyl;
$R^3$ is $R^9$O— or $R^9$NH—, wherein $R^9$ is $C_{1-6}$ alkyl or $C_{3-6}$ cycloalkyl;
$R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;
and or a tautomer thereof;
(b) about 0.1% to 10% by weight of a pharmaceutically acceptable amine or a mixture of pharmaceutically acceptable amines;
(c) about 0.1% to 10% by weight of a pharmaceutically acceptable base or a mixture of pharmaceutically acceptable bases;
(d) one or more pharmaceutically acceptable oils;
(e) optionally one or more pharmaceutically acceptable hydrophilic solvents;
(f) optionally one or more pharmaceutically acceptable polymers; and
(g) optionally one or more pharmaceutically acceptable surfactants;
and wherein the amine component (b) and the base component (c) are not the same compound.

2. A pharmaceutical composition according to claim 1, wherein the compound of formula (I) is present in an amount of from about 1% to 50% by weight.

3. A pharmaceutical composition according to claim 1, wherein the amine is present in an amount of from about 0.5% to 7% by weight.

4. A pharmaceutical composition according to claim 1, wherein the amine is a $C_{1-6}$ alkylamine, di-($C_{1-6}$ alkyl)-amine or tri-($C_{1-6}$ alkyl)-amine, wherein one or more alkyl groups thereof may be optionally substituted by one or more hydroxy groups, or the amine is $C_{1-6}$ alkylenediamine, a basic amino acid or choline hydroxide, or mixtures thereof.

5. A pharmaceutical composition according to claim 1, wherein the amine is selected from ethanolamine, diethanolamine, triethanolamine, tris(hydroxymethyl)aminomethane, ethylenediamine, dimethylaminoethanol, or meglumine, or mixtures thereof.

6. A pharmaceutical composition according to to claim 1, wherein the base is present in an amount of from about 0.1% to 5% by weight.

7. A pharmaceutical composition according to to claim 1, wherein the base is selected from sodium hydroxide, potassium hydroxide, sodium hydrogen carbonate, aluminum hydroxide, magnesium hydroxide; and magnesium aluminum hydroxide.

8. A pharmaceutical composition according to claim 1, wherein the pharmaceutically acceptable oil is present in an amount of from about 20% to 70% by weight.

9. A pharmaceutical composition according to claim 1, wherein the pharmaceutically acceptable oil is selected from: medium or long chain mono-, di- or triglycerides, water insoluble vitamins, fatty acids and mixtures thereof.

10. A pharmaceutical composition according to claim 1, wherein the pharmaceutically acceptable oil is selected from: triglycerides of caprylic fatty acids; triglycerides of capric fatty acids; and mixtures thereof.

11. A pharmaceutical composition according to claim 1, wherein the pharmaceutically acceptable hydrophilic solvent is selected from propylene glycol, polypropylene glycol, polyethylene glycol, glycerol, ethanol, dimethyl isosorbide, glycofurol, propylene carbonate, dimethyl acetamide, water, or mixtures thereof.

12. A pharmaceutical composition according to claim 1, wherein the pharmaceutically acceptable hydrophilic solvent is selected from propylene glycol, polyethylene glycol, ethanol, water, and mixtures thereof.

13. A pharmaceutical composition according to claim 1, wherein the pharmaceutically acceptable polymer is present in an amount of up to about 50% by weight.

14. A pharmaceutical composition according to claim 1, wherein the pharmaceutically acceptable polymer is selected from polyethylene glycols, polyvinylpyrrolidones, polyvinylalcohols, cellulose derivatives, polyacrylates, polymethacrylates, sugars, polyols, and mixtures thereof.

15. A pharmaceutical composition according to claim 1, wherein the pharmaceutically acceptable surfactant is present in an amount of up to about 70% by weight.

16. A pharmaceutical composition according to claim 1, wherein the pharmaceutically acceptable surfactant is selected from d-alpha tocopheryl polyethylene glycol 1000 succinate, polyoxyl castor oils, polysorbates, peglicol 6-oleate, polyoxyethylene stearates, polyglycolyzed glycerides or poloxamers, or sodium lauryl sulfate and mixtures thereof.

17. A pharmaceutical composition according to claim 1, wherein the pharmaceutically acceptable surfactant is selected from d-alpha tocopheryl polyethylene glycol 1000 succinate, polyoxyl 40 hydrogenated castor oil, polyoxyl 35 castor oil, polyoxypropylene-polyoxyethylene block copolymer, or sodium lauryl sulfate, and mixtures thereof.

18. A pharmaceutical composition according to claim 1, wherein in the compound of formula (I):

R¹ is methoxy;

L¹, L² are each independently H;

R² is

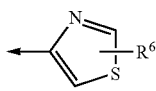

wherein R⁶ is NH—(C₁₋₄alkyl) or NH—(C3-6cycloalkyl);

R³ is R⁹O—, wherein R⁹ is butyl, cyclobutyl or cyclopentyl;

R⁴ is H or C₁₋₆ alkyl;

and following moiety:

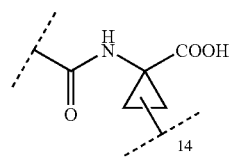

has the configuration represented by the following diastereoisomer:

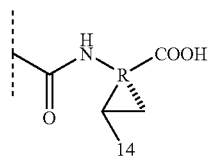

in which configuration position 14 is linked syn to the COOH group.

19. A pharmaceutical composition according to claim 1, wherein the compound of formula (I) is selected from the compounds listed in the following table:

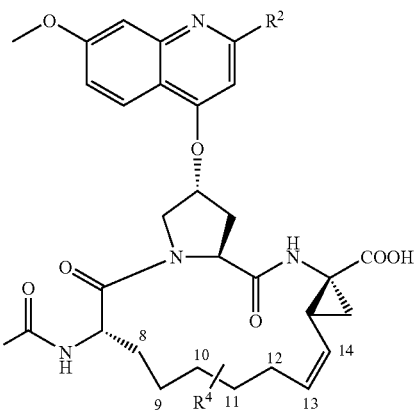

wherein the bond from position 14 to the cyclopropyl group is syn to the COOH, said 13,14 double bond is cis, R³, R⁴ and R² are defined as follows:

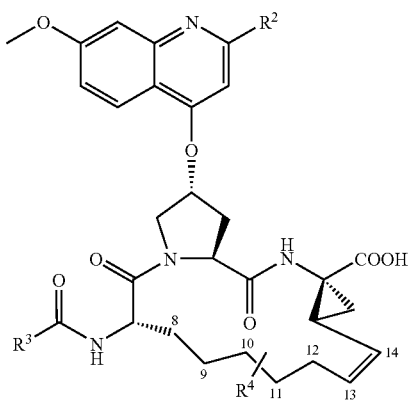

wherein the bond from position 14 to the cyclopropyl group is syn to the COOH, said 13, 14 double bond is cis, R³, R⁴ and R² are defined as follows:

| Cpd # | R³: | R⁴: | R²: |
|---|---|---|---|
| 801 | cyclobutyl-O— | H | thiazolyl-NHC(O)CH₃ |

-continued

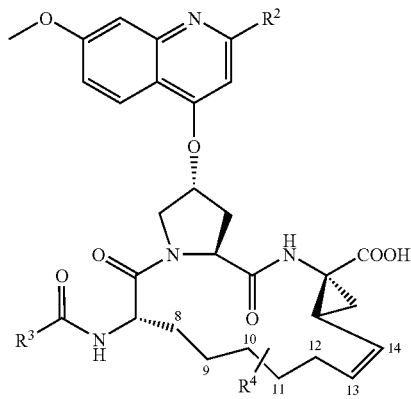

wherein the bond from position 14 to the cyclopropyl group is syn to the COOH, said 13, 14 double bond is cis, $R^3$, $R^4$ and $R^2$ are defined as follows:

| Cpd # | $R^3$: | $R^4$: | $R^2$: |
|---|---|---|---|
| 804 | (S)-N-tBu-CH(CH3)-NH- | H | 2-acetamido-thiazol-4-yl |
| 805 | cyclopentyl-O- | H | pyrrol-1-yl |
| 807 | cyclopentyl-O- | H | OEt |
| 808 | isopropyl-O- | H | OEt |
| 809 | cyclopentyl-O- | H | 2-acetamido-thiazol-4-yl |
| 810 | cyclopentyl-O- | H | 2-ethylamino-thiazol-4-yl |
| 811 | cyclopentyl-O- | H | 2-methylamino-thiazol-4-yl |
| 812 | cyclopentyl-O- | H | 2-amino-thiazol-4-yl |
| 814 | cyclopentyl-O- | H | thiazol-2-yl |

-continued

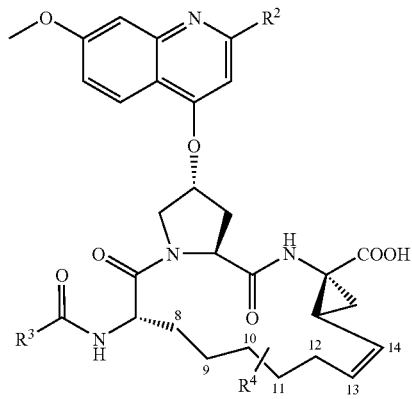

wherein the bond from position 14 to the cyclopropyl group is syn to the COOH, said 13, 14 double bond is cis, $R^3$, $R^4$ and $R^2$ are defined as follows:

| Cpd # | $R^3$: | $R^4$: | $R^2$: |
|---|---|---|---|
| 815 | cyclopentyl-O- | H | pyridin-2-yl |
| 816 | (S)-tert-butyl-CH(CH3)-NH- | H | 2-(ethylamino)thiazol-4-yl |
| 817 | cyclopentyl-O- | H | 4-isopropylthiazol-2-yl |
| 818 | cyclopentyl-O- | H | 2-(methoxycarbonylamino)thiazol-4-yl |
| 819 | cyclopentyl-O- | H | 2-(isobutoxycarbonylamino)thiazol-4-yl |
| 820 | cyclobutyl-O- | H | 2-(ethylamino)thiazol-4-yl |
| 821 | cyclopentyl-O- | H | pyrazol-1-yl |
| 822 | cyclopentyl-O- | H | 2-(isopropylamino)thiazol-4-yl |

-continued

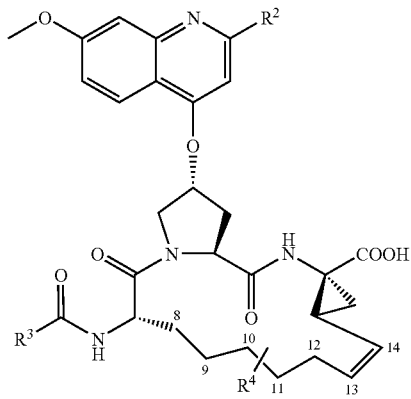

wherein the bond from position 14 to the cyclopropyl group is syn to the COOH, said 13, 14 double bond is cis, R³, R⁴ and R² are defined as follows:

| Cpd # | R³: | R⁴: | R²: |
|---|---|---|---|
| 823 | cyclopentyl-O- | H | pyrazol-3-yl |
| 824 | cyclopentyl-O- | 10-(R) Me | OEt |
| 825 | cyclopentyl-O- | H | 2-(cyclopropylamino)thiazol-4-yl |
| 826 | cyclopentyl-O- | H | 2-(cyclobutylamino)thiazol-4-yl |
| 827 | cyclopentyl-O- | H | 2-(cyclopentylamino)thiazol-4-yl |
| and 828 | cyclopentyl-O- | H | 2-(cyclohexylamino)thiazol-4-yl |

20. A pharmaceutical composition according to claim 19, wherein the compound of formula (I) is compound 822.

21. A pharmaceutical composition according to claim 1, comprising:
   (a) about 5% to 30% by weight of a compound of formula (I);
   (b) about 0.1% to 7% by weight of a pharmaceutically acceptable amine;
   (c) about 0.1% to 5% by weight of a pharmaceutically acceptable base;
   (d) about 1% to 99% by weight of a pharmaceutically acceptable oil;
   (e) up to about 70% by weight of a pharmaceutically acceptable hydrophilic solvent;
   (f) optionally up to about 50% by weight of a pharmaceutically acceptable polymer; and
   (g) up to about 70% by weight of a pharmaceutically acceptable surfactant.

22. A pharmaceutical composition according to claim 1, comprising:
   (a) about 10% to 20% by weight of a compound of formula (I);
   (b) about 0.1% to 5% by weight of a pharmaceutically acceptable amine;

(c) about 0.1% to 3% by weight of a pharmaceutically acceptable base;
(d) about 20% to 70% by weight of a pharmaceutically acceptable oil;
(e) about 10% to 30% by weight of a pharmaceutically acceptable hydrophilic solvent;
(f) optionally about 1% to 20% by weight of a pharmaceutically acceptable polymer; and
(g) about 20% to 50% by weight of a pharmaceutically acceptable surfactant.

23. A pharmaceutical composition according to claim 1, comprising:
(a) about 10% to 20% by weight of a compound of formula (I);
(b) about 0.1% to 5% by weight of tris(hydroxymethyl) aminomethane;
(c) about 0.1% to 3% by weight of sodium hydroxide;
(d) about 20% to 70% by weight of a triglyceride of caprylic fatty acid or a triglyceride of capric fatty acid, or mixtures thereof;
(e) about 10% to 30% by weight of a mixture of propylene glycol, ethanol and optionally water;
(f) optionally about 1% to 20% by weight of polyethylene glycol or polyvinylpyrrolidone; and
(g) about 20% to 50% by weight of d-alpha tocopheryl polyethylene glycol 1000 succinate or polyoxyl 35 castor oil.

24. A pharmaceutical composition according to claim 1, comprising:
(a) about 10% to 15% by weight of a compound of formula (I);
(b) about 0.1% to 2% by weight of tris(hydroxymethyl) aminomethane;
(c) about 0.1% to 1% by weight of sodium hydroxide;
(d) about 20% to 30% by weight of medium chain mono- and diglycerides or medium chain triglyceride;
(e) about 15% to 25% by weight of a mixture of propylene glycol, ethanol and water;
(f) about 40% to 50% by weight of d-alpha tocopheryl polyethylene glycol 1000 succinate; and
(g) about 0.01% to 1% of dl-α-tocopherol.

25. A pharmaceutical composition according to claim 1, in the form of a fluid dosage form selected from a hard shell or sofigel capsule or in the form of a solid dosage form selected from a powder, a tablet or a capsule.

26. A pharmaceutical composition according to claim 1, further comprising one or more antioxidants.

27. A method of manufacturing a pharmaceutical composition according to claim 1, said method comprising: p1 (a) mixing together the pharmaceutically acceptable oil(s), surfactant(s) and solvent(s); (b) dissolving the pharmaceutically acceptable amine(s), base(s) and polymer(s) in the mixture obtained in step (a); (c) optionally heating the mixture obtained in step (b) if necessary to sufficiently melt one or more of the components of the mixture; (d) adding the compound of formula (I) to the mixture obtained in steps (b) or (c) and mixing.

28. A method of inhibiting the replication of hepatitis C virus by exposing the virus to a hepatitis C viral NS3 protease inhibiting amount of the composition according to claim 1.

29. A method of treating a hepatitis C viral infection in a mammal comprising administering to a mammal in need thereof a therapeutically effective amount of the composition according to claim 1.

* * * * *